US012778480B2

(12) United States Patent
Somayajula

(10) Patent No.: US 12,778,480 B2
(45) Date of Patent: Nov. 3, 2026

(54) SMART DEVICE LED ECG

(71) Applicant: AliveCor, Inc., Mountain View, CA (US)

(72) Inventor: Siva Somayajula, Saratoga, CA (US)

(73) Assignee: AliveCor, Inc., Mountain View, CA (US)

( * ) Notice: Subject to any disclaimer, the term of this patent is extended or adjusted under 35 U.S.C. 154(b) by 132 days.

(21) Appl. No.: 17/387,613

(22) Filed: Jul. 28, 2021

(65) Prior Publication Data

US 2023/0037187 A1 Feb. 2, 2023

(51) Int. Cl.
*A61B 5/327* (2021.01)
*A61B 5/00* (2006.01)

(52) U.S. Cl.
CPC ............ *A61B 5/327* (2021.01); *A61B 5/0006* (2013.01); *A61B 5/0022* (2013.01); *A61B 5/7225* (2013.01); *A61B 5/749* (2013.01)

(58) Field of Classification Search
CPC ..... A61B 5/327; A61B 5/0006; A61B 5/0022; A61B 5/7225; A61B 5/749
See application file for complete search history.

(56) References Cited

U.S. PATENT DOCUMENTS 11,158,426 B1 * 10/2021 Lo .......................... G16H 50/20
2002/0095093 A1 * 7/2002 Au .......................... A61B 5/332 600/509
2009/0216142 A1 * 8/2009 Stelzer .................. A61B 5/282 600/509
2014/0378781 A1 * 12/2014 Peluso .................... A61B 5/01 600/301
2015/0018660 A1 * 1/2015 Thomson ............... A61B 5/332 600/393
2016/0135701 A1 * 5/2016 Drake .................... A61B 5/332 600/523
2017/0265806 A1 * 9/2017 Albert .................... A61B 5/318
2018/0211656 A1 * 7/2018 Chong .................... G10L 15/22
2019/0046036 A1 * 2/2019 Ogino .................. A61B 5/7282
2019/0274574 A1 * 9/2019 Hughes ................ A61B 5/0006
2021/0154487 A1 * 5/2021 Bongberg .............. G16H 20/30

* cited by examiner

*Primary Examiner* — Niketa Patel
*Assistant Examiner* — Moussa Haddad
(74) *Attorney, Agent, or Firm* — Womble Bond Dickinson (US) LLP

(57) ABSTRACT

Embodiments of the present disclosure provide systems and methods for providing an audio user interface by which a user may be provided audio instructions for measuring physiological parameters using a monitoring device as well as an audio explanation of the results of analysis of the physiological parameters. A cloud service may receive via a smart device a voice command associated with measuring physiological parameters and provide to the smart device, instructions for measuring the physiological parameters. The monitoring device is configured to communicate with the cloud service via the smart device, which may provide the instructions for taking the ECG using the ECG monitoring device to a user as an audio output. The cloud service may receive physiological parameter data measured by the monitoring device and process the data to provide a set of interpretations of the data as well as audio data corresponding to a simplified explanation thereof.

14 Claims, 9 Drawing Sheets

SMART DEVICE LED ECG

TECHNICAL FIELD

The present disclosure relates to medical devices, systems, and methods and in particular, to systems for providing an audio user interface which can facilitate the taking of an ECG and provide an easy to understand interpretation of the results.

BACKGROUND

Cardiovascular diseases are the leading cause of death in the world. In 2008, 30% of all global death can be attributed to cardiovascular diseases. It is also estimated that by 2030, over 23 million people will die from cardiovascular diseases annually. Cardiovascular diseases are prevalent across populations of first and third world countries alike, and affect people regardless of socioeconomic status.

Arrhythmia is a cardiac condition in which the electrical activity of the heart is irregular or is faster (tachycardia) or slower (bradycardia) than normal. Although many arrhythmias are not life-threatening, some can cause cardiac arrest and even sudden cardiac death. Indeed, cardiac arrhythmias are one of the most common causes of death when travelling to a hospital. Atrial fibrillation (A-fib) is the most common cardiac arrhythmia. In A-fib, electrical conduction through the ventricles of heart is irregular and disorganized. While A-fib may cause no symptoms, it is often associated with palpitations, shortness of breath, fainting, chest pain or congestive heart failure and also increases the risk of stroke. A-fib is usually diagnosed by taking an electrocardiogram (ECG) of a subject. To treat A-fib, a person may take medications to slow heart rate or modify the rhythm of the heart. Persons may also take anticoagulants to prevent stroke or may even undergo surgical intervention including cardiac ablation to treat A-fib. In another example, an ECG may provide decision support for Acute Coronary Syndromes (ACS) by interpreting various rhythm and morphology conditions, including Myocardial Infarction (MI) and Ischemia.

An ECG provides a number of waveforms that represent the electrical activity of a person's heart. An ECG monitoring device may comprise a set of electrodes for recording these waveforms (also referred to herein as "taking an ECG") of the person's heart. A typical heartbeat may include several variations of electrical potential, which may be classified into waves and complexes, including a P wave, a QRS complex, a T wave, and a U wave among others, as is known in the art. The shape and duration of these waves may be related to various characteristics of the person's heart such as the size of the person's atrium (e.g., indicating atrial enlargement) and can be a first source of heartbeat characteristics unique to a person. ECG waveforms may be analyzed for various indicators that are useful in detecting cardiac events or status, such as cardiac arrhythmia detection and characterization.

Often, a person with A-fib (or other type of arrhythmia) is monitored for extended periods of time to manage the disease. The American Heart Association and the European Society of Cardiology recommends that a 12-lead ECG should be acquired as early as possible for people with possible ACS when symptoms present. Prehospital ECG has been found to significantly reduce time-to-treatment and shows better survival rates. The time-to-first-ECG is so vital that it is a quality and performance metric monitored by several regulatory bodies. According to the national health statistics for 2015, over 7 million people visited the emergency department (ED) in the United States (U.S.) with the primary complaint of chest pain or related symptoms of ACS. In the US, ED visits are increasing at a rate of or 3.2% annually and outside the U.S. ED visits are increasing at 3% to 7%, annually.

As a result of this, there are a number of ECG devices which can provide ECG monitoring on an ad-hoc basis to continuously monitor the electrical activity of a user's cardiovascular system. These devices range from larger form factor devices such as Holter monitors to smaller form factor devices such as smartwatches and handheld portable ECG monitors etc. Many of these devices are capable of synchronizing with a computing device (e.g., laptop, smart phone, etc.) so as to transmit recorded waveforms to the computing device for storage and display.

However, analysis of an ECG waveform is difficult for a layperson having no training in electrophysiology. In most cases, a physician or other medical personnel highly trained in electrophysiology must analyze and interpret the waveforms in order to determine the person's cardiac status. Thus, even if an ECG can be taken on an ad-hoc basis using portable ECG monitoring devices, most users cannot understand and interpret the resulting waveforms and cannot determine if they are suffering or may potentially be suffering from a serious cardiac condition. Although many computing devices that synchronize with ECG monitors can transmit their waveform data to a physician or other healthcare provider of the user, there can be a significant delay in obtaining results.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

DETAILED DESCRIPTION

It is to be understood that the present disclosure is not limited in its application to the details of construction, experiments, exemplary data, and/or the arrangement of the components set forth in the following description. The embodiments of the present disclosure are capable of other embodiments or of being practiced or carried out in various ways. Also, it is to be understood that the terminology employed herein is for purpose of description and should not be regarded as limiting.

In the following detailed description of embodiments of the present disclosure, numerous specific details are set forth in order to provide a more thorough understanding of the disclosure. However, it will be apparent to one of ordinary skill in the art that the concepts within the disclosure can be practiced without these specific details. In other instances, well-known features have not been described in detail to avoid unnecessarily complicating the description.

An electrocardiogram (ECG) provides a number of ECG waveforms that represent the electrical activity of a person's heart. An ECG monitoring device may comprise a set of electrodes for recording these ECG waveforms (also referred to herein as "taking an ECG") of the person's heart. The set of electrodes may be placed on the skin of the person in multiple locations and the electrical signal (ECG waveform) recorded between each electrode pair in the set of electrodes may be referred to as a lead. Varying numbers of leads can be used to take an ECG, and different numbers and combinations of electrodes can be used to form the various leads. Example numbers of leads used for taking ECGs are 1, 2, 6, and 12 leads.

The ECG waveforms (each one corresponding to a lead of the ECG) recorded by the ECG monitoring device may comprise data corresponding to the electrical activity of the person's heart. A typical heartbeat may include several variations of electrical potential, which may be classified into waves and complexes, including a P wave, a QRS complex, a T wave, and a U wave among others, as is known in the art. Stated differently, each ECG waveform may include a P wave, a QRS complex, a T wave, and a U wave among others, as is known in the art. The shape and duration of these waves may be related to various characteristics of the person's heart such as the size of the person's atrium (e.g., indicating atrial enlargement) and can be a first source of heartbeat characteristics unique to a person. The ECG waveforms may be analyzed (typically after standard filtering and "cleaning" of the signals) for various indicators that are useful in detecting cardiac events or status, such as cardiac arrhythmia detection and characterization. Such indicators may include ECG waveform amplitude and morphology (e.g., QRS complex amplitude and morphology), R wave-ST segment and T wave amplitude analysis, and heart rate variability (HRV), for example.

Figure 1A:
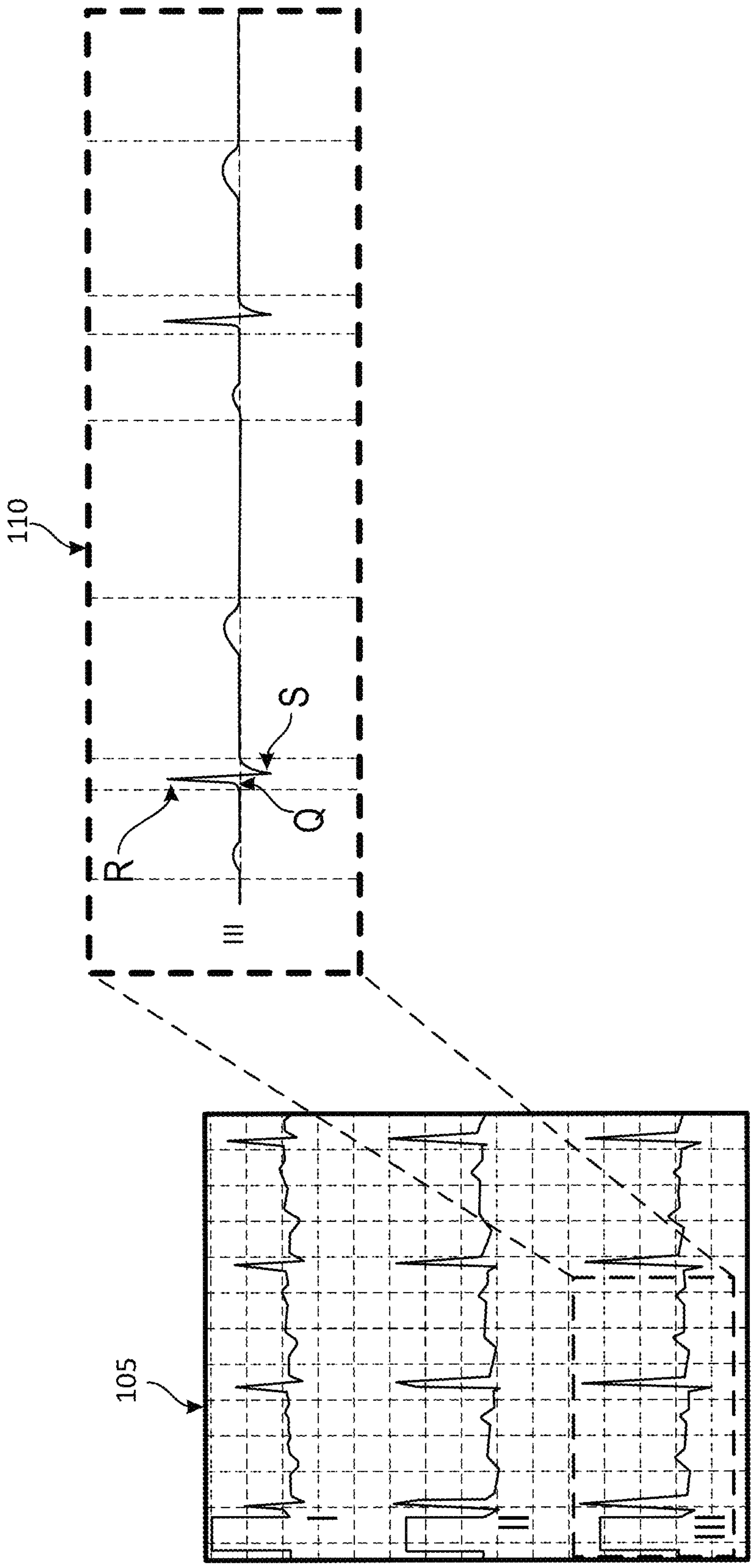
FIG. 1A is a diagram illustrating electrocardiogram (ECG) waveforms, in accordance with some embodiments of the present disclosure.

As noted above, ECG waveforms are generated from measuring multiple leads (each lead formed by a different electrode pair), and the ECG waveform obtained from each different electrode pair/lead may be different/unique (e.g., may have different morphologies/amplitudes). This is because although the various leads may analyze the same electrical events, each one may do so from a different angle. FIG. 1A illustrates a view 105 of an ECG waveform detected by each of 3 leads (I, II, and III) when a 3-lead ECG is taken as well as an exploded view 110 of the ECG waveform measured by lead III illustrating the QRS complex. As shown, the amplitudes and morphologies of the ECG waveform taken from leads I-III are all different, with the ECG waveform measured by lead III having the largest amplitude and the ECG waveform measured by lead I having the smallest amplitude.

There are different "standard" configurations for electrode placement that can be used to place electrodes on the person. For example, an electrode placed on the right arm can be referred to as RA. The electrode placed on the left arm can be referred to as LA. The RA and LA electrodes may be placed at the same location on the left and right arms, preferably near the wrist in some embodiments. The leg electrodes can be referred to as RL for the right leg and LL for the left leg. The RL and LL electrodes may be placed on the same location for the left and right legs, preferably near the ankle in some embodiments. Lead I is typically the voltage between the left arm (LA) and right arm (RA), e.g. I=LA−RA. Lead II is typically the voltage between the left leg (LL) and right arm (RA), e.g. II=LL−RA. Lead III is the typically voltage between the left leg (LL) and left arm (LA), e.g. III=LL−LA. Augmented limb leads can also be determined from RA, RL, LL, and LA. The augmented vector right (aVR) lead is equal to RA−(LA+LL)/2 or −(I+II)/2. The augmented vector left (aVL) lead is equal to LA—(RA+LL)/2 or I−II/2. The augmented vector foot (aVF) lead is equal to LL−(RA+LA)/2 or II−I/2.

Figure 1B:
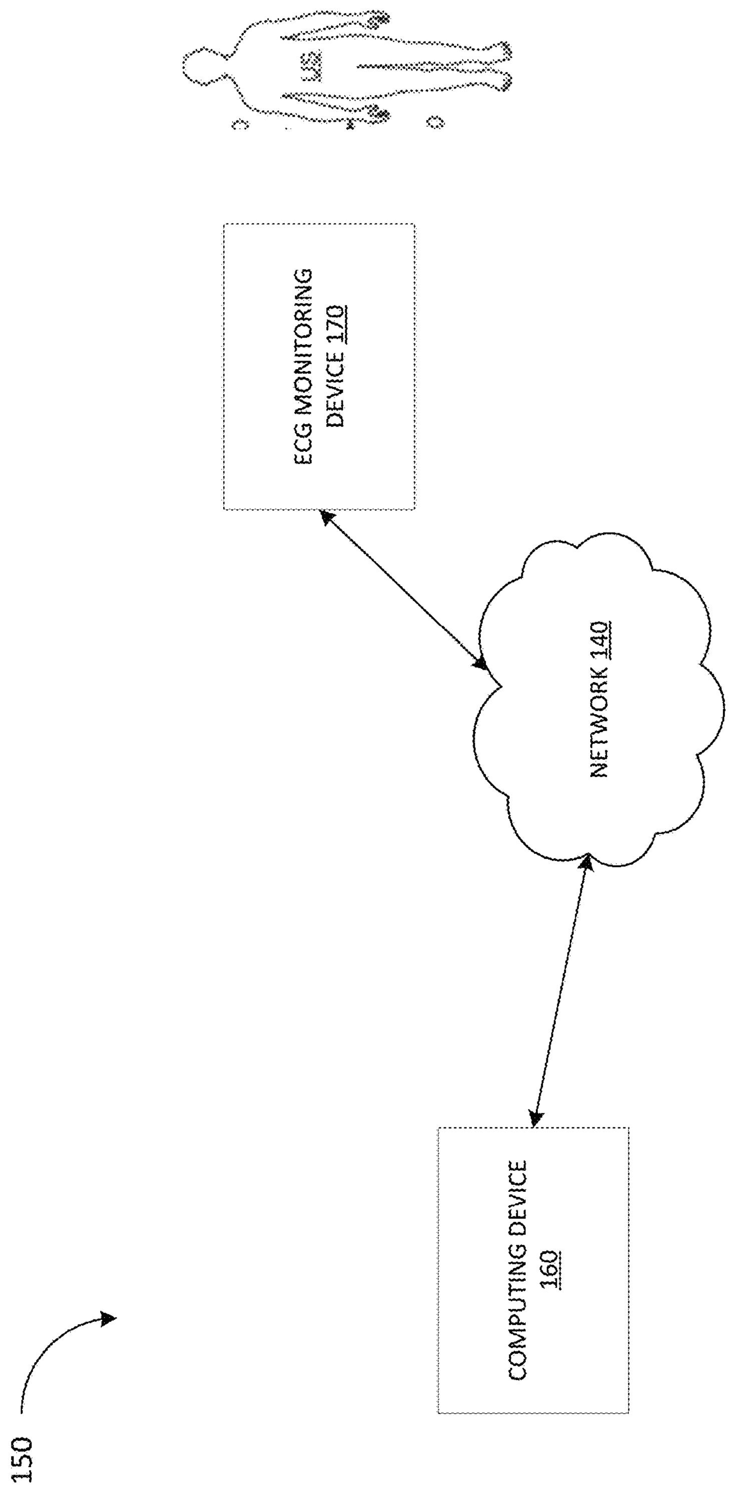
FIG. 1B illustrates a system, in accordance with some embodiments of the present disclosure.

FIG. 1B illustrates a system 150 for measuring and monitoring one or more biometric or physiological parameters of a user. The system 150 may comprise a computing device 160 and a monitoring device 170. The computing device 160 and monitoring device 170 may be coupled to each other (e.g., may be operatively coupled, communicatively coupled, may communicate data/messages with each other) via network 140. Network 140 may be a public network (e.g., the internet), a private network (e.g., a local area network (LAN) or wide area network (WAN)), or a combination thereof. In one embodiment, network 140 may include a wired or a wireless infrastructure, which may be provided by one or more wireless communications systems, such as a WiFi' hotspot connected with the network 140 and/or a wireless carrier system that can be implemented using various data processing equipment, communication towers (e.g. cell towers), etc. In some embodiments, the network 140 may be an L3 network. In other embodiments, the network 140 may alternatively or in combination comprise a BlueTooth connection, a low power BlueTooth connection, an NFC (near field communication) connection, a near field ultrasound communication connection, or any other appropriate connection. The network 140 may carry communications (e.g., data, message, packets, frames, etc.) between computing device 160 and the monitoring device 170. In some embodiments, the computing device 160 and the monitoring device 170 may be connected by a wired connection (not shown) such as a universal serial bus (USB) connection, a Firewire connection, a Lightning connection, or the like.

The computing device 160 may include hardware (not shown) such as processing devices (e.g., processors, central processing units (CPUs)), memory (e.g., random access memory (RAM), storage devices (e.g., hard-disk drive (HDD), solid-state drive (SSD), etc.)), a network interface configured to connect with network 140, and other hardware devices (e.g., sound card, video card, etc.). In some embodiments, the memory may be a persistent storage that is capable of storing data. A persistent storage may be a local storage unit or a remote storage unit. Persistent storage may be a magnetic storage unit, optical storage unit, solid state storage unit, electronic storage units (main memory), or similar storage unit. Persistent storage may also be a monolithic/single device or a distributed set of devices. The memory may be configured for long-term storage of data and may retain data between power on/off cycles of the computing device 160. The computing device 160 may comprise any suitable type of computing device or machine that has a programmable processor including, for example, server computers, desktop computers, laptop computers, tablet computers, smartphones, set-top boxes, etc. In some examples, the computing device 160 may comprise a single machine or may include multiple interconnected machines (e.g., multiple servers configured in a cluster). The computing device 160 may further comprise other components (not shown) such as motion detection components, one or more cameras, additional displays, power supplies, fans, various I/O ports, etc.

The Monitoring device 170 may comprise similar elements as the computing device 160 as well as a sensor 180. The sensor 180 is configured to couple with the user US through any appropriate connection such as physical contact for example, to sense or detect one or more physiological parameters of the user US. Generally, the one or more physiological parameters comprises a cardiac parameter such as of a heart rate, a heart rate variability, a blood pressure, a blood pressure variability, an arrhythmia, a seisomocardiogram (SCG), an SCG parameter, an electrocardiogram (ECG), or an ECG parameter, electromyogram (EMG), electrooculogram (EOG), pulse oximetry, photoplethysmogram (PPG) and/or electroencephalogram (EEG) parameter of the user. For example, the sensor 180 may comprise a set of electrodes (not shown) for measuring ECG waveforms as discussed above. Other physiological parameters are also contemplated. For example, the sensor 180 may comprise an activity sensor, a blood glucose sensor, a blood oxygenation sensor, a thermometer, a respiratory sensor, a metabolic sensor, an odor detector, or the like. The processor of the monitoring device 170 may receive the detected physiological parameter and process it into a signal which may be transmitted to the computing device 160 via network 140.

In some embodiments, the monitoring device 170 may be removably coupled to the computing device 160 and may comprise a cover for covering the computing device 160, such as a tablet computer case or a smartphone case or cover. In this manner, the monitoring device 170 may not need to be replaced as the user replaces or upgrades his or her computing device 160. That is, the same monitoring device 170 may be used by the user for the different computing devices 160 the user may have.

In some embodiments, the monitoring device 170 may comprise an ambulatory ECG device such as a Holter monitor, or other similar device which may include a set of electrodes (e.g., 10 electrodes) in order to measure a full 12-lead ECG. The processing device of the Monitoring device 170 may process the ECG waveform measured at each lead to generate a set of ECG signals and transmit the ECG signals to the computing device 160.

In some embodiments, the monitoring device 170 may comprise a handheld ECG monitor (such as the KardiaMobile® or KardiaMobile® 6L device from AliveCor® Inc., for example) comprising a smaller number of electrodes (e.g., 2 or 3 electrodes). In these embodiments, the electrodes can be used to measure a subset of the leads described above, such as lead I (e.g., the voltage between the left arm and right arm) contemporaneously with lead II (e.g., the voltage between the left leg and right arm), and lead I contemporaneously with lead V2 or another one of the chest leads such as V5. It should be noted that any other combination of leads is possible. In some embodiments, the monitoring device 170 may be in the form of a smartphone, or a wearable device such as a smart watch. In some embodiments, the monitoring device 170 may be a handheld sensor coupled to the computing device 160 with an intermediate protective case/adapter. The processing device of the monitoring device 170 may transmit the ECG waveforms corresponding to the measured subset of leads to the computing device 160 via network 140.

The computing device 160 may receive the detected physiological parameter(s) and perform one or more analyses on the physiological parameter(s). For example, the computing device 160 may perform standard filtering and "cleaning" of the signals corresponding to the physiological parameter(s). In another example where the monitoring device 10 is an ECG monitoring device, the computing device 160 may algorithmically derive additional leads from the determined subset of leads. For example, augmented limb leads can also be determined from the values measured by the LA, RA, LL, and RL electrodes. The augmented vector right (aVR) may be equal to RA−(LA+LL)/2 or −(I+II)/2. The augmented vector left (aVL) may be equal to LA−(RA+LL)/2 or I−II/2. The augmented vector foot (aVF) may be equal to LL−(RA+LA)/2 or II−I/2. In yet another example, the computing device 160 may utilize a machine learning (ML) model to derive a full 12 lead set from the ECG waveforms corresponding to the measured subset of leads. It should be noted that in some embodiments, one or more of the above analyses may be performed by the processing device of the monitoring device 170 itself and the resulting signals may be transmitted to the computing device 160.

The computing device 160 may time-stamp and tag the received physiological parameter(s) with user identify information for later access and analysis and store the received physiological parameter(s) in the memory. The computing device 160 may also display the physiological parameters on its display. In some embodiments, the physiological parameters may be displayed in real-time as they are measured/processed. The computing device 160 may also include functionality for analyzing the physiological data to determine/detect one or more conditions and present the interpretations and analysis to the user US. Furthermore, the computing device 160 may transmit the physiological data to a remote computing device, a remote server, or a remote healthcare provider such as a physician, nurse, or hospital automatically via the network 140.

However, signals corresponding to physiological parameters are not easily understood by lay people. In the example of an ECG, an ECG waveform is difficult for a layperson having no training in electrophysiology to understand. In most cases, a physician or other medical personnel highly trained in electrophysiology must analyze and interpret the waveforms in order to determine the person's cardiac status. Thus, even if an ECG can be taken on an ad-hoc basis using portable ECG monitoring devices, most users cannot understand and interpret the resulting waveforms and cannot determine if they are suffering or may potentially be suffering from a serious cardiac condition. Although many computing devices that synchronize with ECG monitors can transmit their waveform data to a physician or other healthcare provider of the user, there can be a significant delay in obtaining results.

Figure 2A:
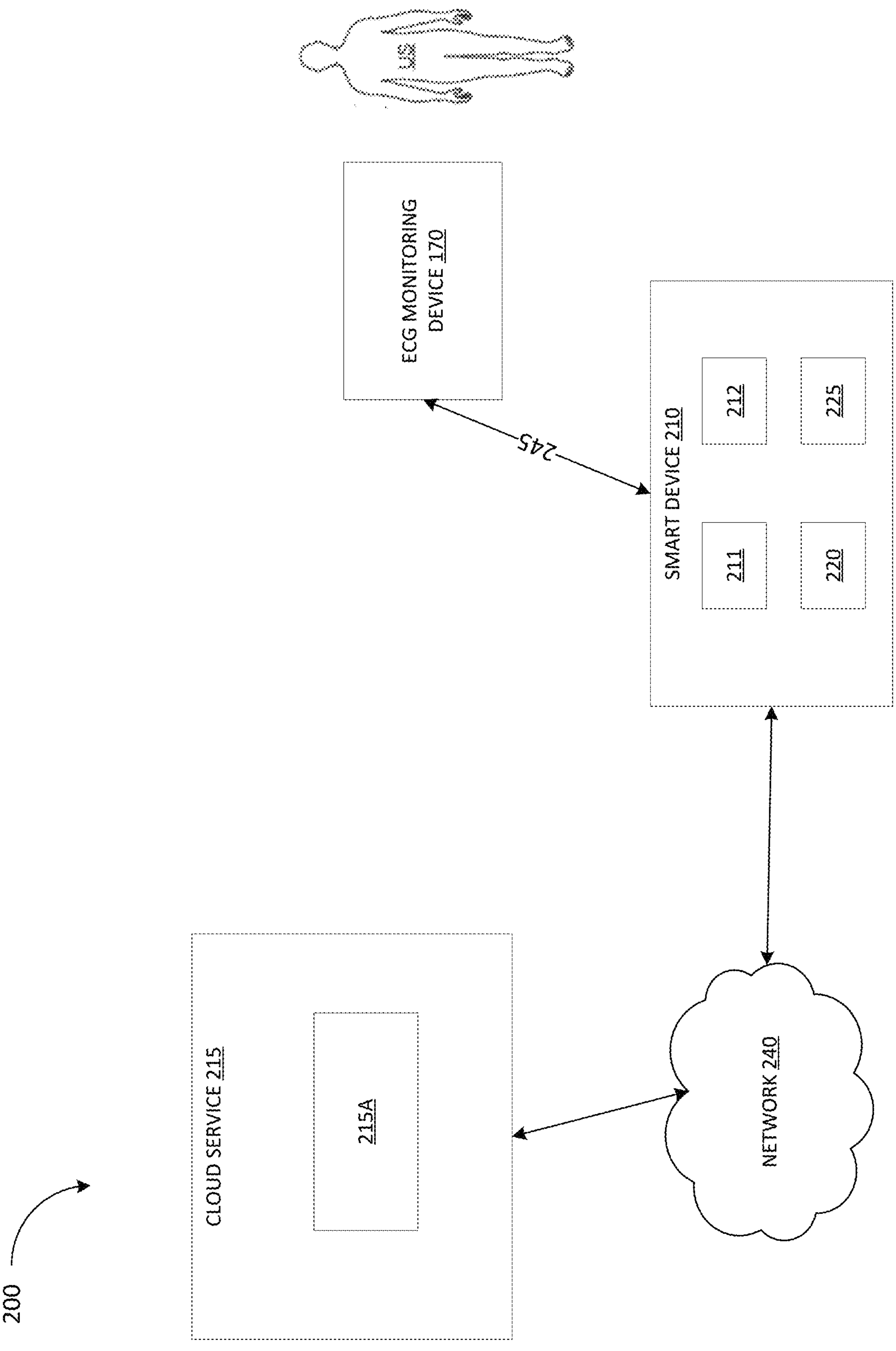
FIG. 2A illustrates a system, in accordance with some embodiments of the present disclosure.

FIG. 2A illustrates a system 200 in accordance with some embodiments of the present disclosure. The system 200 may comprise the monitoring device 170 of FIG. 1B, a smart device 210, and a cloud service 215. The smart device 210 may be a computing device that includes hardware such as a processing device 211 (e.g., processors, central processing units (CPUs)), a memory 212 (e.g., random access memory (RAM)), storage devices (e.g., hard-disk drive (HDD), solid-state drive (SSD), etc.), a microphone 220, speakers 225, and other hardware devices (e.g., transceiver—not shown). In some embodiments, the memory 212 may be a persistent storage that is capable of storing data. A persistent storage may be a local storage unit or a remote storage unit. Persistent storage may be a magnetic storage unit, optical storage unit, solid state storage unit, electronic storage units (main memory), or similar storage unit. Persistent storage may also be a monolithic/single device or a distributed set of devices. The memory 212 may be configured for long-term storage of data and may retain data between power on/off cycles of the smart device 210. The smart device 210 may comprise e.g., an Amazon™ Echo™ smart speaker, a home automation controller, or other similar device.

The smart device 210 may function to facilitate communication between the monitoring device 170 and the cloud service 215 as discussed in further detail herein, and may also utilize the speakers 225 and information received from the cloud service 215 to provide a voice user interface (UX) as also described in further detail herein. In this way, upon receiving voice commands from the user via the microphone 220, the smart device 210 may route the voice commands to the cloud service 215. The cloud service 215 and the smart device 210 may communicate via network 240, which may be a public network (e.g., the internet), a private network (e.g., a local area network (LAN) or wide area network (WAN)), or a combination thereof. In one embodiment, network 240 may include a wired or a wireless infrastructure, which may be provided by one or more wireless communications systems, such as a WiFi' hotspot connected with the network 240 and/or a wireless carrier system that can be implemented using various data processing equipment, communication towers (e.g. cell towers), etc. In some embodiments, the network 240 may be an L3 network.

The cloud service 215 may comprise a plurality of interconnected computing devices (e.g., multiple servers configured in a cloud storage cluster). Each computing device of the cloud service 215 may include components similar to computing device 160 of FIG. 1B and may comprise any suitable type of computing device or machine that has a programmable processor including, for example, a server computer, a desktop computer, laptop computer, tablet computer, smartphone, etc. As discussed in further detail herein, the cloud service 215 may provide natural language processing functionality to determine an intent from voice commands issued by the user to the smart device 210. For example, the user may request to perform an ECG by uttering a phrase such as "Alexa, take an ECG." This utterance may be detected by the microphone 220 and sent to the processing device 211, which may route the utterance to the cloud service 215 (e.g., via a transceiver of the smart device 210 and the network 240).

In some embodiments, when an utterance (e.g., "Alexa, take an ECG") is detected by the microphone 220 and sent to the processing device 205, the processing device 205 may process the utterance itself and determine that the user wishes to take an ECG, and communicate with the cloud service 215 in order to facilitate taking of the ECG.

As shown in FIG. 2A, the cloud service 215 may include an ECG module 215A which may include logic to provide instructions for taking an ECG, monitoring received ECG data, providing updated ECG taking instructions to the user as necessary based on such monitoring, as well as ECG data analysis and interpretation functionality. Although embodiments of the present disclosure are described with reference to the example of an ECG for ease of description, this is not limiting and the embodiments described herein may be applied to provide a voice UX to interpret signals for any number of appropriate physiological parameters. The ECG module 215A may be a software module provided/operated by a healthcare company (e.g., that has provided the monitoring device 170). The user may have a personal account associated with the ECG module 215A (i.e., an account with the healthcare company e.g., AliveCor™) and a cloud services account with the cloud service 215. The cloud services account and personal account of the user may be linked in the cloud services 215 in order to facilitate provision of the functions of the ECG module 215A.

When the user wishes to take an ECG, they may ask the smart device 210 for assistance by uttering a phrase e.g., "Alexa, I want to take an ECG." The microphone 220 of the smart device 210 may detect this phrase and route it to the processor 211 which may route the phrase to the cloud service 215 via a transceiver of the smart device 210 and network 240. The cloud service 215 may receive the phrase and utilize its natural language processing functionality to determine that the user wishes to take an ECG. The cloud service 215 may transmit an indication of the user's intent (to take an ECG) to the ECG module 215A, which may begin providing instructions to the user via the smart device 210.

Indeed, instead of communicating with the ECG module 215A directly, the monitoring device 170 may include software/code to implement it as a device that is linked to the ECG module 215A via a compatible device that the monitoring device 170 interacts with, such as the smart device 210. For example, the monitoring device 170 may be implemented as an Alexa™ Gadget, that may use the directives and events defined by Alexa™ Gadgets interfaces to exchange information with the ECG module 215A (via the smart device 210). Continuing the example where the monitoring device 170 is implemented as an Alexa™ Gadget, the ECG module 215A may be implemented as an Alexa™ skill (hosted by cloud service 215), which may trigger certain behavior by the monitoring device 170 and act on information it receives from the monitoring device 170 (via the smart device 210). This communication may be based on a defined custom interface which may utilize a custom interface controller to access information from the ECG module 215A. The smart device 210 may facilitate all such communications between the ECG module 215A and the monitoring device 170.

In some embodiments, one or more of the smart device 210 and the monitoring device 170 may have dedicated software or firmware to allow them to communicate with each other. For example, the monitoring device 170 may be built with software or firmware (e.g., a special purpose driver) that enables it to communicate with the smart device 210, which can subsequently route communications and information received from the monitoring device 170 to the ECG module 215A. The smart device 210 and the monitoring device 170 may communicate via communication channel 245, which may comprise a BlueTooth connection, a low power BlueTooth connection, an NFC (near field communication) connection, a near field ultrasound communication connection, an infrared connection, an audio connection, or any other appropriate connection.

Figure 2B:
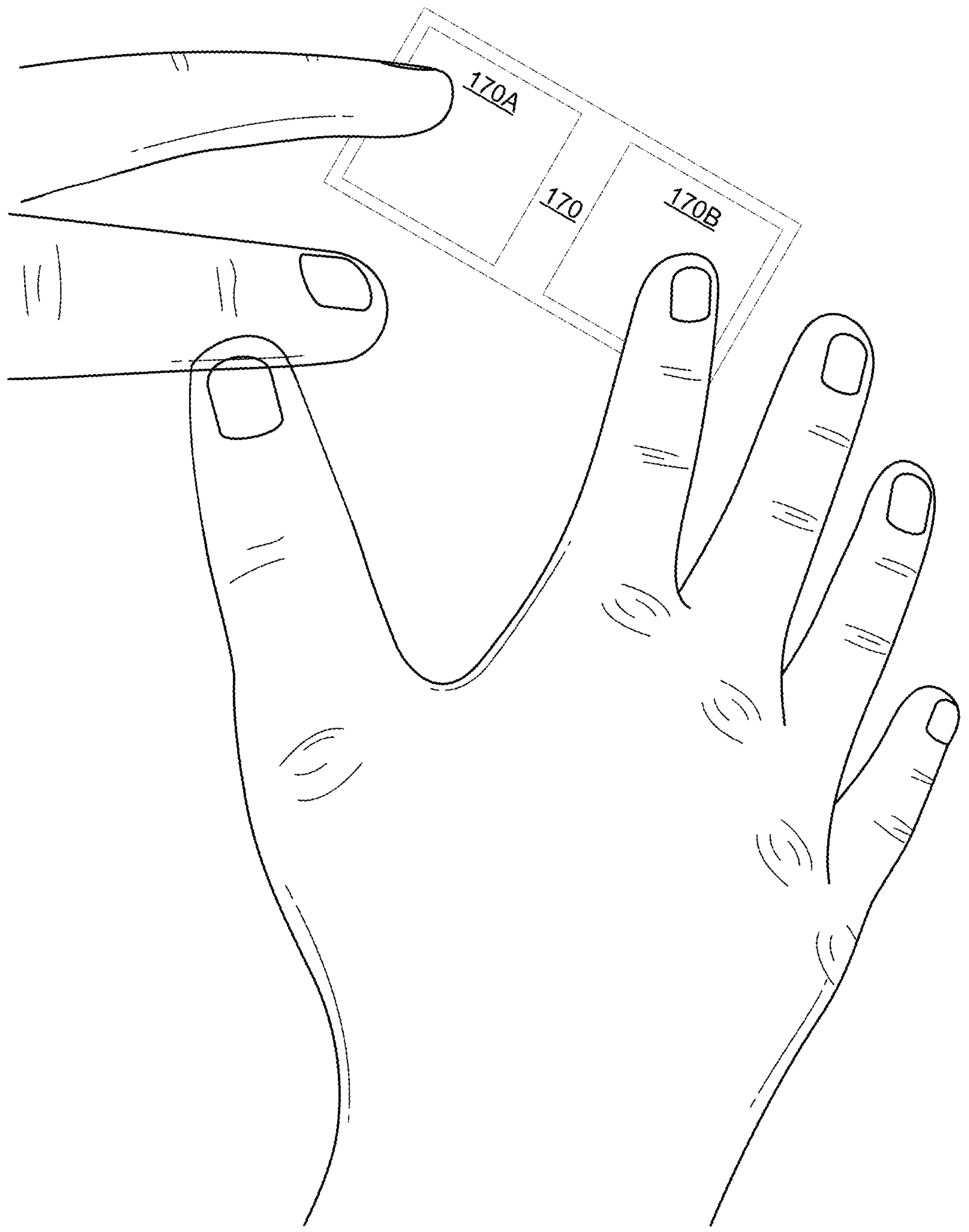
FIG. 2B illustrates a positioning of an ECG monitoring device on a user, in accordance with some embodiments of the present disclosure.

The smart device 210 may provide the instructions for taking an ECG received from the ECG module 215A as audio output in order to instruct the user to take an ECG using the monitoring device 170. More specifically, the smart device 210 may (based on the instructions received from the ECG module 215A) instruct the user to contact the monitoring device 170 as shown in FIG. 2B so as to take a single lead ECG. More specifically, the smart device 210 may instruct the user to contact the monitoring device 170 as shown in FIG. 2B, such that the user's left arm (e.g., respective fingers of the user's left hand) are contacting electrode 170A. The smart device 210 may then instruct the user to contact the monitoring device 170 as shown in FIG. 2B, such that the user's right arm (e.g., respective fingers of the user's right hand) is simultaneously contacting the electrode 170B so as to take a single lead (e.g., lead I) ECG. When the user is in the correct position, the monitoring device 170 may begin taking an ECG of the user over a time period specified by the ECG module 215A in the instructions and transmitting (as it is captured) the ECG data corresponding to the measured ECG signals of the user over the time period to the ECG module 215A via the smart device 210. As the ECG module 215A receives ECG data, it may analyze the received ECG data to determine whether the ECG is being taken correctly (e.g., whether the user is maintaining the correct position on each electrode 170A and 170B). For example, analysis of the ECG data for a first portion of the prescribed time period by the ECG module 215A may indicate that the user is maintaining the correct position. However, ECG data of a subsequent portion may indicate that the user removed one or more fingers from the electrodes prematurely or moved their fingers such that measurement of the ECG was interfered with. If the ECG data indicates that the user is not correctly positioned, the ECG module 215A may provide instructions to cease the current measuring and retake the ECG to the user. The instructions for retaking the ECG may include instructions on how to adjust the positioning of one or more appendages relative to the electrodes as necessary, for example.

Figure 2C:
FIG. 2C illustrates a positioning of an ECG monitoring device on a user, in accordance with some embodiments of the present disclosure.

FIG. 2C illustrates an example contact position of the user with the monitoring device 170 after receiving instructions from the smart device 210 when the monitoring device 170 comprises 3 electrodes. The smart device 210 may (based on the instructions received from the ECG module 215A) instruct the user to contact the monitoring device 170 as shown in FIG. 2C so as to take a 2-lead ECG. More specifically, the smart device 210 may instruct the user to contact the monitoring device 170 such that the user's left arm (left hand) is contacting electrode 170A. The smart device 210 may then instruct the user to contact the monitoring device 170 such that the user's right arm (right hand) is contacting the electrode 170B. Subsequently, the smart device 210 may instruct the user to contact the monitoring device 170 such that the user's left leg is contacting the electrode 170C so as to take a 2-lead (e.g., leads I and II) ECG. When the user is in the correct position, the monitoring device 170 may begin taking an ECG of the user over a time period specified by the ECG module 215A and transmitting (as it is captured) the ECG data corresponding to the measured ECG signals of the user over the time period to the ECG module 215A via the smart device 210. As the cloud service 215 (and more specifically, the ECG module 215A) receives ECG data, it may analyze the received ECG data to determine whether the ECG is being taken correctly (e.g., whether the user is maintaining the correct position). If the ECG data indicates that the user is not correctly positioned, it may provide instructions to retake the ECG to the user including how to adjust the positioning of one or more appendages relative to the electrodes as necessary.

Upon receiving the ECG data measured by the monitoring device 170 for the entire time period from the smart device 210, the ECG module 215A may perform certain processing of the ECG data. The ECG module 215A may include ECG signal processing, algorithm and AI based lead generation, and waveform interpretation functionality. In this way, the ECG module 215A may perform any necessary signal filtering, error correction, cleaning, and transforming, generate additional leads as required/necessary, and perform ECG signal interpretation and diagnosis to generate a set of interpretations based on the processed ECG data.

The cloud service 215 may generate audio data corresponding to a simplified explanation of the set of interpretations and may transmit the set of interpretations and the audio data corresponding to the simplified explanation back to the smart device 210, where the processor 211 may generate an audio output corresponding to the simplified explanation and provide the audio output to the user via the speaker 225. For example, the smart device 210 may use the speakers 225 to output audio indicating that the user's sinus rhythms and heart beat are normal. In another example, the smart device 210 may use the speakers 225 to output audio indicating that the user has a slight arrhythmia and that a follow up consultation with the user's physician is recommended. In some embodiments, based on the set of interpretations, when the cloud service 215 transmits the results back to the smart device 210, it may also include instructions for the smart device 210 to transmit one or more of an alert that an ECG was performed, the set of interpretations (as well as the ECG data itself in some embodiments), and an alert regarding a serious cardiac condition (if one is detected) to one or more of: a physician/health care provider of the user, a family member/emergency contact of the user, and emergency medical services (and/or any other appropriate third party). In some embodiments, the smart device 210 may transmit the above information to a third party via a mobile computing device (e.g., computing device 160 as shown in FIG. 3) by transmitting the alert and the set of interpretations to the computing device along with instructions to forward the alert and the set of interpretations to the third party.

In some embodiments, the ECG module 215A may instruct the user to take an ECG at regular intervals (e.g., thrice daily, daily, weekly etc.) and may provide reminders for the user to do so. The ECG module 215A may also maintain a calendar for the user indicating particular dates/times when the ECG is to be taken and provide alerts (via the smart device 210) to the user when the time for taking an ECG is approaching.

As discussed herein, the smart device 210 may generate audio output indicating the results of the ECG module 215A's analysis of the ECG data in a simplified manner that a lay person can understand, so that the user may have a more informed understanding of their cardiac status as well as what additional steps need to be taken, if any. The smart device 210 may also instruct the user on how to take an effective ECG without the need for a display as if the smart device 210 provides a way to communicate to the monitoring device 170 directly.

Figure 3:
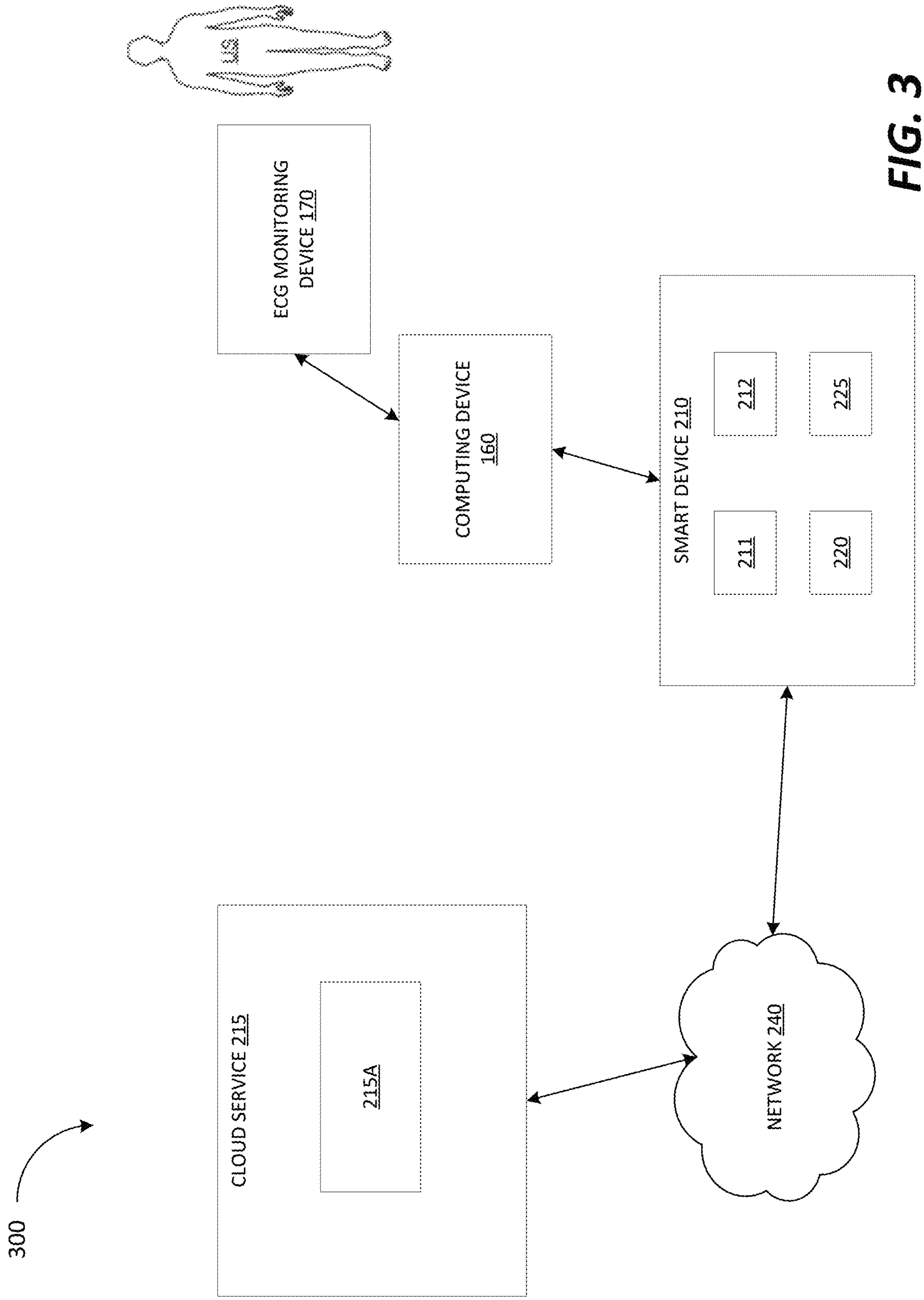
FIG. 3 illustrates a system, in accordance with some embodiments of the present disclosure.

FIG. 3 illustrates a system 300 in accordance with some embodiments of the present disclosure. System 300 may be similar to system 150, but may include a computing device 160 (e.g., as described in FIG. 1B). The computing device 160 may already be synchronized with the smart device 210 as well as the monitoring device 170, and thus may function to route communications between the smart device 210 and the monitoring device 170. More specifically, the computing device 160 may function to translate communications received from the monitoring device 170 and transmit them to the smart device 210, which may then function to facilitate communication with cloud service 215 (and more specifically, the ECG module 215A) as described with respect to FIG. 2A. In some embodiments, the computing device 160 may also function to synchronize the user's personal and cloud services accounts to help facilitate communication between the ECG module 215A and the monitoring device 170. In addition, when transmitting a set of interpretations and audio data corresponding thereto back to the smart device 210, the ECG module 215A may include an indication for the smart device 210 to store the set of interpretations and the audio data on the computing device 160. In this way, the user may have the capability to search through their ECG data history on an ad-hoc basis.

Figure 4:
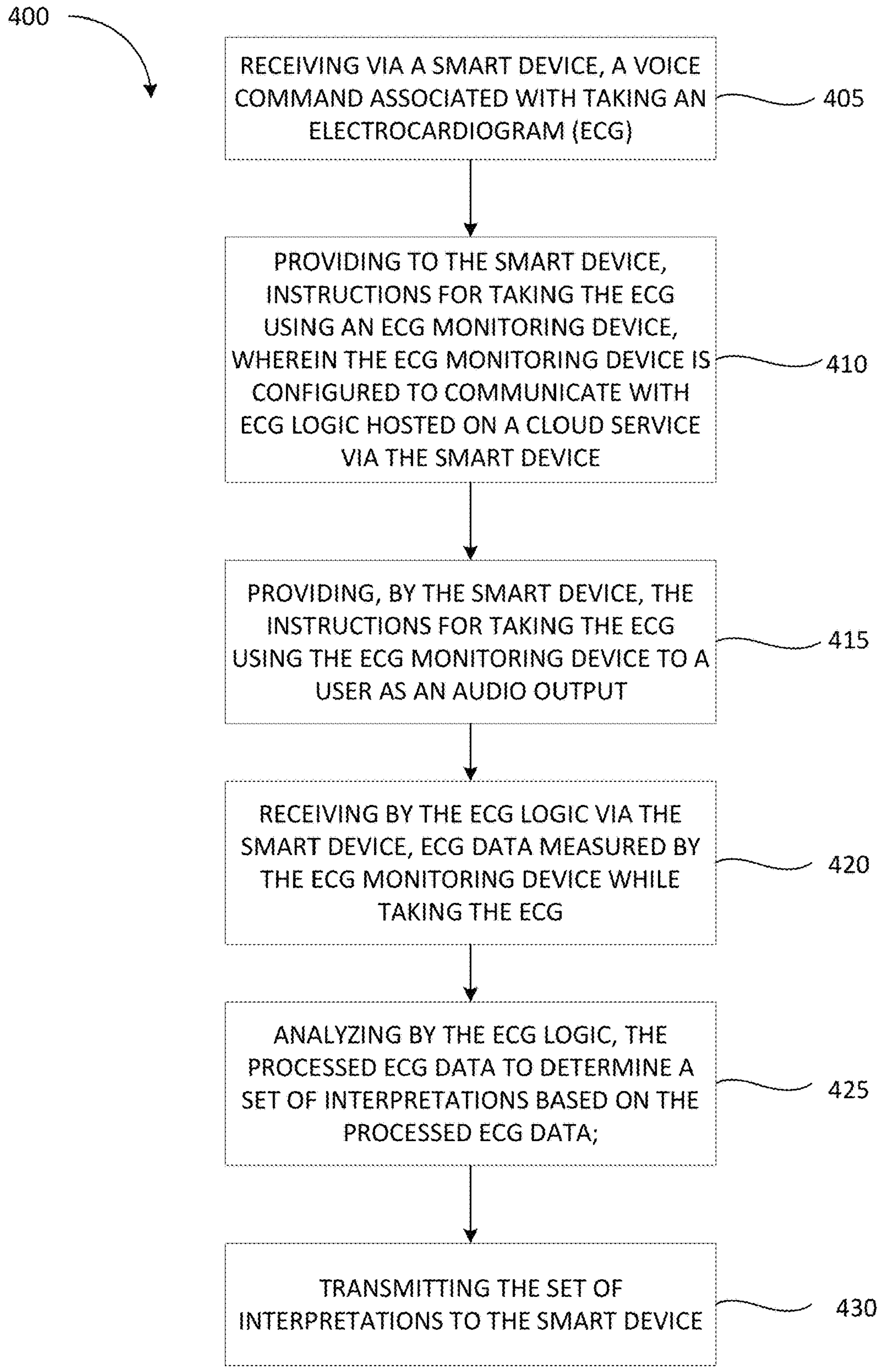
FIG. 4 is a flow diagram of a method for providing an audio user interface through which a user of the ECG monitoring device of FIG. 2A can be instructed on how to take an ECG as well as receive ECG results and interpretations, in accordance with some embodiments of the present disclosure.

FIG. 4 is a flow diagram of a method 400 for providing an audio UX through which a user of monitoring device 170 can be instructed to take an ECG and receive ECG results and interpretations, in accordance with some embodiments of the present disclosure. Method 400 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 400 may be performed by one or more computing devices (e.g., system 200 illustrated in FIG. 2A).

Referring simultaneously to FIG. 2A, when a user wishes to take an ECG, they may ask the smart device 210 for assistance by uttering a phrase e.g., "Alexa, I want to take an ECG." At block 405, the microphone 220 of the smart device 210 may detect this phrase and route it to the processor 211 which may route the phrase to the cloud service 215 via a transceiver of the smart device 210 and network 240. The cloud service 215 may receive the phrase and utilize its natural language processing functionality to determine that the user wishes to take an ECG. The cloud service 215 may transmit an indication of the user's intent (to take an ECG) to the ECG module 215A, which may begin providing instructions to the user via the smart device 210 at block 410.

Indeed, instead of communicating with the ECG module 215A directly, the monitoring device 170 may include software/code to implement it as a device that is linked to the ECG module 215A via a compatible device that the monitoring device 170 interacts with, such as the smart device 210. For example, the monitoring device 170 may be implemented as an Alexa™ Gadget, that may use the directives and events defined by Alexa™ Gadgets interfaces to exchange information with the ECG module 215A (via the smart device 210). Continuing the example where the monitoring device 170 is implemented as an Alexa™ Gadget, the ECG module 215A may be implemented as an Alexa™ skill (hosted by cloud service 215), which may trigger certain behavior by the monitoring device 170 and act on information it receives from the monitoring device 170 (via the smart device 210). This communication may be based on a defined custom interface which may utilize a custom interface controller to access information from the ECG module 215A. The smart device 210 may facilitate all such communications between the ECG module 215A and the monitoring device 170.

In some embodiments, one or more of the smart device 210 and the monitoring device 170 may have dedicated software or firmware to allow them to communicate with each other. For example, the monitoring device 170 may be built with software or firmware (e.g., a special purpose driver) that enables it to communicate with the smart device 210, which can subsequently route communications and information received from the monitoring device 170 to the ECG module 215A. The smart device 210 and the monitoring device 170 may communicate via communication channel 245, which may comprise a BlueTooth connection, a low power BlueTooth connection, an NFC (near field communication) connection, a near field ultrasound communication connection, an infrared connection, an audio connection, or any other appropriate connection.

At block 415, the smart device 210 may provide audio output instructing the user to take an ECG using the monitoring device 170. More specifically, the smart device 210 may (based on the instructions received from the ECG module 215A) instruct the user to contact the monitoring device 170 as shown in FIG. 2B so as to take a single lead ECG. More specifically, the smart device 210 may instruct the user to contact the monitoring device 170 as shown in FIG. 2B, such that the user's left arm (e.g., respective fingers of the user's left hand) are contacting electrode 170A. The smart device 210 may then instruct the user to contact the monitoring device 170 as shown in FIG. 2B, such that the user's right arm (e.g., respective fingers of the user's right hand) is simultaneously contacting the electrode 170B so as to take a single lead (e.g., lead I) ECG. When the user is in the correct position, the monitoring device 170 may begin taking an ECG of the user over a time period specified by the ECG module 215A and at block 420, may begin transmitting (as it is captured) the ECG data corresponding to the measured ECG signals of the user over the time period to the ECG module 215A via the smart device 210.

Figure 5:
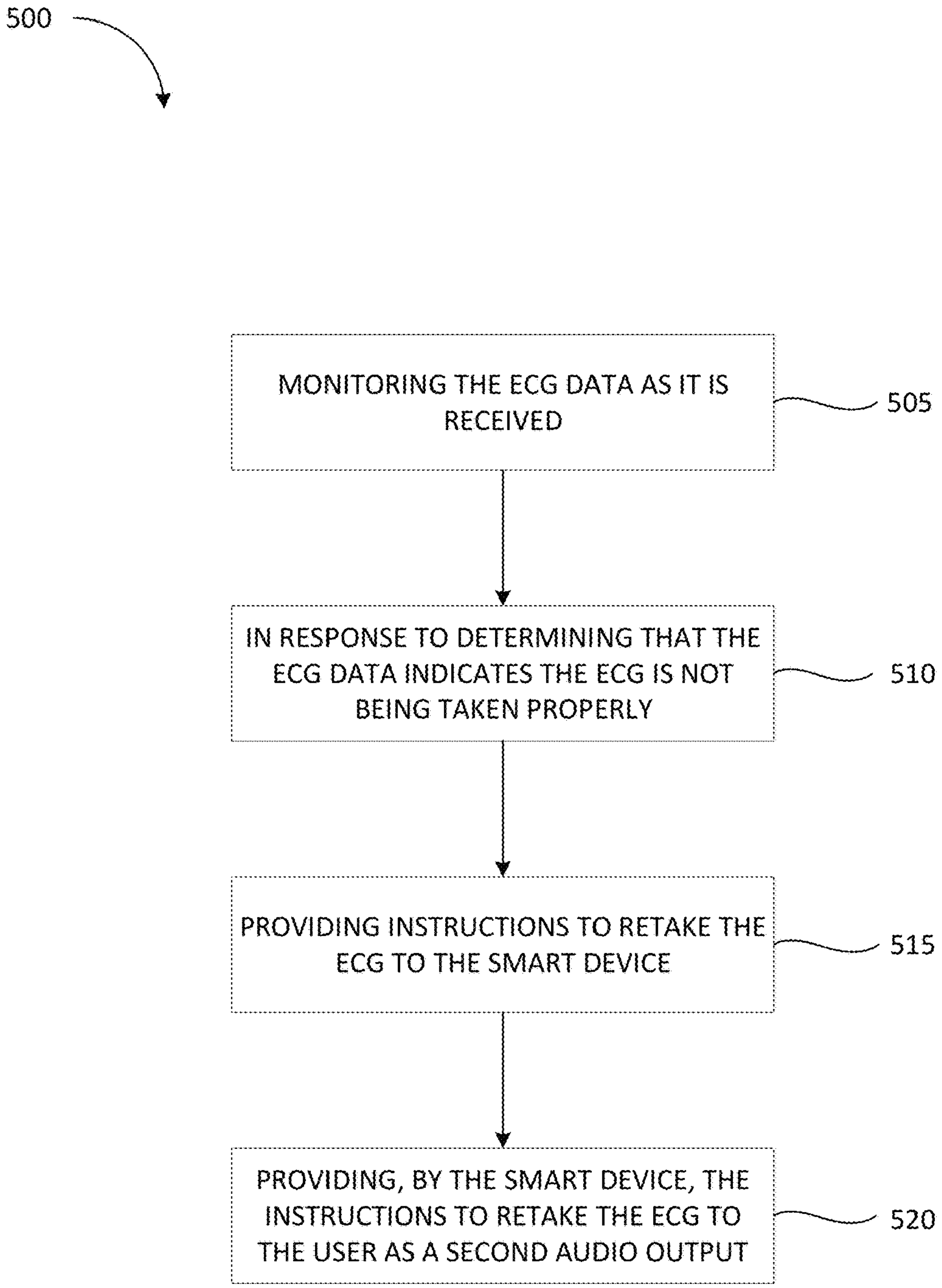
FIG. 5 is a flow diagram of a method for monitoring whether a user is taking an ECG with the ECG monitoring device of FIG. 2A properly and providing an audio user interface through which the user can be instructed to retake the ECG when the ECG is not being taken properly, in accordance with some embodiments of the present disclosure.

FIG. 5 is a flow diagram of a method 500 of ensuring that an ECG was taken properly, in accordance with some embodiments of the present disclosure. Method 500 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 500 may be performed by one or more computing devices (e.g., system 200 illustrated in FIG. 2A).

As the cloud service 215 (and more specifically, the ECG module 215A) receives ECG data, at block 505, it may monitor the received ECG data to determine whether the ECG is being taken correctly (e.g., whether the user is maintaining the correct position). The ECG data indicates that the user is not correctly positioned. For example, analysis of the ECG data for a first portion of the prescribed time period may indicate that the user is maintaining the correct position. However, ECG data of a subsequent portion may indicate that the user removed one or more fingers from the electrodes prematurely or moved their fingers such that measurement of the ECG was interfered with. At block 510, in response to determining that the ECG is not being taken correctly, the ECG module 215A may at block 515 provide to the smart device 210, instructions to retake the ECG including how to adjust the positioning of one or more appendages relative to the electrodes as necessary. At block 520, the smart device 210 may provide the instructions to retake the ECG to the user as an audio output via speakers 220.

Referring back to FIG. 4, upon receiving the ECG data measured by the monitoring device 170 for the entire time period from the smart device 210, at block 425 the ECG module 215A may process the ECG data using one or more functions and generate a set of interpretations from the ECG data. The ECG module 215A may include ECG signal processing, algorithm and AI based lead generation, and waveform interpretation functionality, for example. In this way, the cloud service 215 may perform any necessary signal filtering, error correction, cleaning, and transforming, generate additional leads as required/necessary, and perform ECG signal interpretation and diagnosis to generate a set of results.

At block 430, the cloud service 215 may transmit the results back to the smart device 210, where the processor 211 may generate audio signals corresponding to the results and provide the audio signals to the user via the speaker 225. For example, the smart device 210 may use the speakers 225 to output an audio diagnosis indicating that the user's sinus rhythms and heart beat are normal. In another example, the smart device 210 may use the speakers 225 to output an audio diagnosis indicating that the user had a slight arrhythmia. In some embodiments, based on the severity of the diagnosis, when the cloud service 215 transmits the results back to the smart device 210, it may also include instructions for the smart device 210 to alert one or more of: a health care provider, an emergency contact, and emergency medical services.

In some embodiments, the ECG module 215A may instruct the user to take an ECG at regular intervals (e.g., thrice daily, daily, weekly etc.) and may provide reminders for the user to do so. The ECG module 215A may also maintain a calendar for the user indicating particular dates/times when the ECG is to be taken and provide alerts (via the smart device 210) to the user when the time for taking an ECG is approaching.

Figure 6:
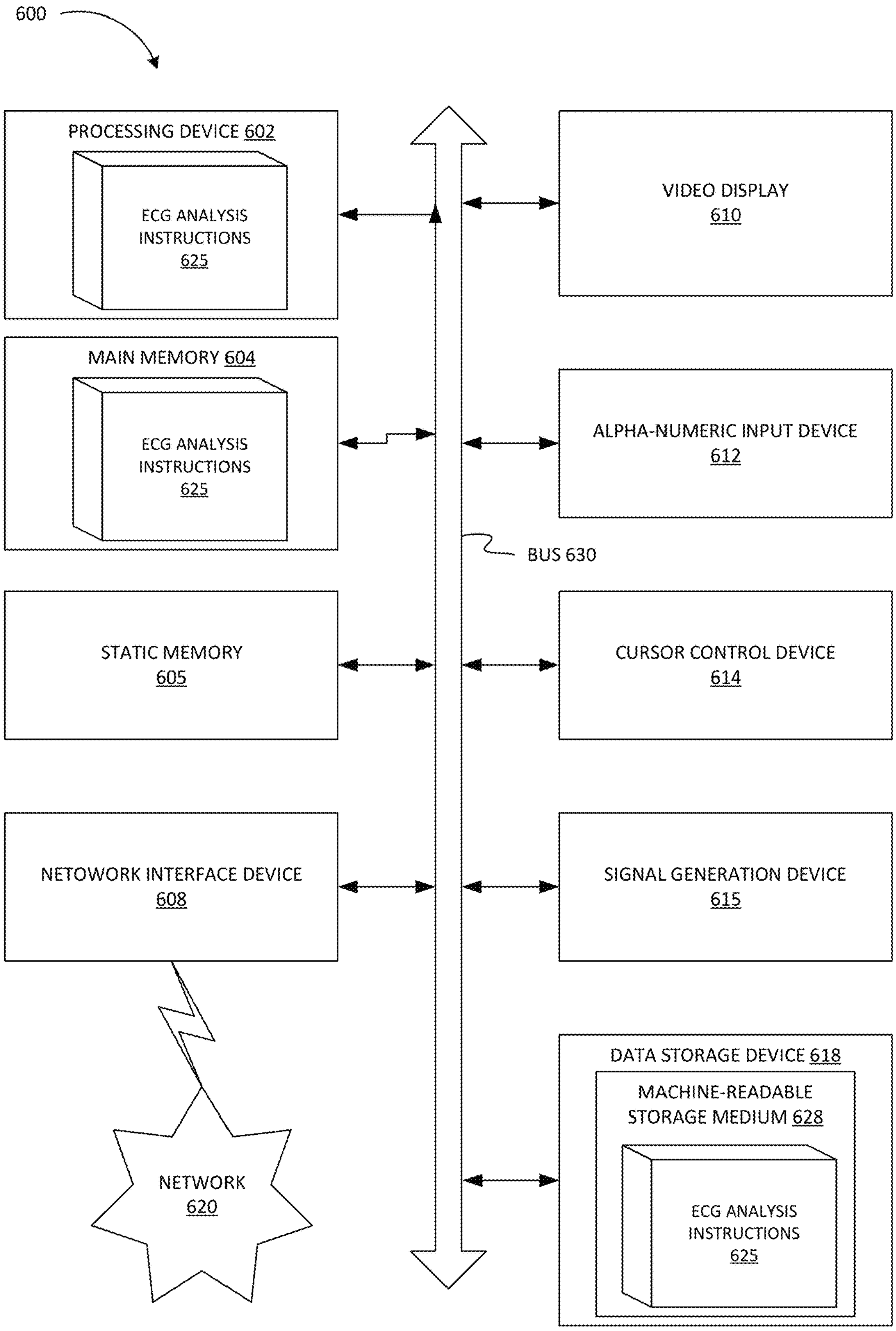
FIG. 6 is a block diagram of an example computing device that may perform one or more of the operations described herein, in accordance with some embodiments of the present disclosure.

FIG. 6 illustrates a diagrammatic representation of a machine in the example form of a computer system 600 within which a set of instructions, for causing the machine to perform any one or more of the embodiments discussed herein.

In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 600 may be representative of a server.

The exemplary computer system 600 includes a processing device 602, a main memory 704 (e.g., read-only memory (ROM), flash memory, dynamic random access memory (DRAM), a static memory 606 (e.g., flash memory, static random access memory (SRAM), etc.), and a data storage device 618, which communicate with each other via a bus 630. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Computing device 600 may further include a network interface device 608 which may communicate with a network 620. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse) and an acoustic signal generation device 616 (e.g., a speaker). In one embodiment, video display unit 610, alphanumeric input device 612, and cursor control device 614 may be combined into a single component or device (e.g., an LCD touch screen).

Processing device 602 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute ECG analysis instructions 625, for performing the operations and steps discussed herein.

The data storage device 615 may include a machine-readable storage medium 628, on which is stored one or more sets of ECG analysis instructions 625 (e.g., software) embodying any one or more of the methodologies of functions described herein. The ECG analysis instructions 625 may also reside, completely or at least partially, within the main memory 604 or within the processing device 602 during execution thereof by the computer system 600; the main memory 604 and the processing device 602 also constituting machine-readable storage media. The ECG analysis instructions 625 may further be transmitted or received over a network 620 via the network interface device 608.

While the machine-readable storage medium 628 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof

What is claimed is:

1. A method comprising:

receiving via a smart device, a voice command associated with taking an electrocardiogram (ECG) and providing the voice command to ECG logic hosted on a cloud service;

specifying, by the ECG logic, a time period for taking the ECG;

providing, via the ECG logic, instructions for taking the ECG using an ECG monitoring device to the smart device, wherein the ECG monitoring device and the ECG logic each comprise logic to communicate with each other, via the smart device using a set of directives and events, and wherein the instructions indicate, to the ECG monitoring device, a position for taking the ECG;

transmitting the time period from the ECG logic to the smart device in the instructions such that the ECG monitoring device begins to take the ECG according to the time period upon detecting the position by the ECG monitoring device;

providing, by the smart device, the instructions for taking the ECG using the ECG monitoring device as an audio output;

transmitting to the ECG logic via the smart device, ECG data measured by the ECG monitoring device using the set of directives and events;

analyzing by the ECG logic, the measured ECG data to determine a set of interpretations based on the measured ECG data;

monitoring the measured ECG data as it is received to determine whether the ECG is being taken properly;

in response to determining that the measured ECG data indicates the ECG is not being taken properly, providing, via the smart device, instructions for retaking the ECG as a second audio output, wherein the instructions for retaking the ECG include instructions for repositioning one or more appendages relative to electrodes of the ECG monitoring device; and in response to providing the instructions for retaking the ECG, receiving via the smart device, updated measured ECG data indicating the ECG is being taken properly.

2. The method of claim 1, further comprising:

processing by the ECG logic, the measured ECG data in accordance with one or more functions to generate processed ECG data, wherein the ECG logic analyzes the processed ECG data to determine the set of interpretations;

transmitting the set of interpretations to the smart device; and providing, by the smart device, the set of interpretations as a second audio output.

3. The method of claim 2, wherein processing the measured ECG data in accordance with the one or more functions comprises:

performing filtering, error correction, and transformation of the measured ECG data; and generating one or more additional leads based on the measured ECG data.

4. The method of claim 2, wherein the ECG data measured by the ECG monitoring device while taking the ECG is received at the smart device via a mobile device that is in communication with the smart device.

5. The method of claim 4, further comprising:

transmitting the set of interpretations to the mobile device.

6. The method of claim 1, wherein the smart device is a smart speaker.

7. A system comprising:

an electrocardiogram (ECG) monitoring device;

a smart device to receive a voice command associated with taking an electrocardiogram (ECG) and transmit the voice command to ECG logic; and a cloud service that hosts the ECG logic, the cloud service configured to:

receive the voice command;

specify, a time period for taking the ECG;

provide, via the ECG logic, instructions for taking the ECG using the ECG monitoring device to the smart device, wherein the ECG monitoring device and the ECG logic each comprise logic to communicate with each other via the smart device using a set of directives and events, wherein in response to receiving the instructions for taking the ECG using the ECG monitoring device, the smart device is to provide the instructions for taking the ECG using the ECG monitoring device as an audio output, wherein the instructions indicate, to the ECG monitoring device, a position for taking the ECG;

transmit the time period from the ECG logic to the smart device in the instructions such that the ECG monitoring device begins to take the ECG according to the time period upon detecting the position by the ECG monitoring device;

receive, via the smart device, ECG data measured by the ECG monitoring device using the set of directives and events;

analyze using the ECG logic, the measured ECG data to determine a set of interpretations based on the measured ECG data;

transmit the set of interpretations to the smart device;

monitor the measured ECG data as it is received to determine whether the ECG is being taken properly;

in response to determining that the measured ECG data indicates the ECG is not being taken properly, provide instructions for retaking the ECG as a second audio output via the smart device, wherein the instructions for retaking the ECG include instructions for repositioning one or more appendages relative to electrodes of the ECG monitoring device; and in response to providing the instructions for retaking the ECG, receive via the smart device, updated measured ECG data indicating the ECG is being taken properly.

8. The system of claim 7, wherein the smart device is further to:

provide the set of interpretations as a second audio output.

9. The system of claim 7, wherein the cloud service is further to:

process the measured ECG data in accordance with one or more functions to generate processed ECG data, wherein the cloud service analyzes the processed ECG data to generate the set of interpretations based on the ECG data.

10. The system of claim 9, wherein to process the measured ECG data in accordance with the one or more functions, the cloud service is to:

perform filtering, error correction, and transformation of the measured ECG data; and generate one or more additional leads based on the measured ECG data.

11. The system of claim 9, further comprising:

a mobile device in communication with the smart device, wherein the ECG data measured by the ECG monitoring device is received at the smart device via the mobile device.

12. The system of claim 11, wherein the smart device is further to:

transmit the one or more interpretations to the mobile device.

13. The system of claim 7, wherein the smart device is a smart speaker.

14. The system of claim 7, wherein the smart device is a home automation controller.

* * * * *